(12) United States Patent
Lin et al.

(10) Patent No.: US 10,497,350 B2
(45) Date of Patent: Dec. 3, 2019

(54) ARRANGEMENT AND ULTRASONIC, FLOW MEASURING DEVICE

(71) Applicant: Endress + Hauser Flowtec AG, Reinach (CH)

(72) Inventors: Yaoying Lin, Freising (DE); Alfred Rieder, Landshut (DE); Wolfgang Drahm, Erding (DE); Michal Bezdek, Aesch (CH); Pierre Ueberschlag, Saint-Louis (FR)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 297 days.

(21) Appl. No.: 15/563,646

(22) PCT Filed: Mar. 24, 2016

(86) PCT No.: PCT/EP2016/056594
§ 371 (c)(1),
(2) Date: Oct. 2, 2017

(87) PCT Pub. No.: WO2016/169729
PCT Pub. Date: Oct. 27, 2016

(65) Prior Publication Data
US 2018/0075832 A1    Mar. 15, 2018

(30) Foreign Application Priority Data

Apr. 24, 2015 (DE) .................. 10 2015 106 352

(51) Int. Cl.
*G10K 11/00* (2006.01)
*G01F 1/66* (2006.01)
*G01N 29/22* (2006.01)

(52) U.S. Cl.
CPC ............ *G10K 11/002* (2013.01); *G01F 1/662* (2013.01); *G01F 1/667* (2013.01); *G01F 1/665* (2013.01); *G01N 29/222* (2013.01)

(58) Field of Classification Search
CPC .......... G01F 1/662; G01F 1/667; G01F 1/665; G01K 11/002; G01N 29/222
See application file for complete search history.

(56) References Cited

U.S. PATENT DOCUMENTS 3,891,869 A * 6/1975 Scarpa ...................... G01F 1/66
                                                        310/325
4,063,457 A * 12/1977 Zekulin ............... G01F 23/2961
                                                        73/290 V (Continued)

FOREIGN PATENT DOCUMENTS

DE         44 43 415 A1    6/1996
DE         199 51 874 A1   5/2001

(Continued)

OTHER PUBLICATIONS

German Search Report, German PTO, Munich, dated Jan. 5, 2016.

(Continued)

*Primary Examiner* — Jonathan M Dunlap
(74) *Attorney, Agent, or Firm* — Bacon & Thomas, PLLC

(57) ABSTRACT

An arrangement, comprising a housing wall, an ultrasonic transducer and a damping element with a longitudinal axis, which damping element connects the ultrasonic transducer with the housing wall. The ultrasonic transducer has an end piece with a medium-contacting surface, from which ultrasonic signals are transferred into a gaseous or liquid medium. The damping element is provided for body sound damping between the ultrasonic transducer and the housing wall, and wherein the damping element has at least one, especially a number of, oscillatory nodes, characterized in that there is arranged between the damping element and the (Continued)

housing wall at least a first sealing ring, which is positioned at a height of an oscillatory node.

11 Claims, 2 Drawing Sheets

(56) References Cited

U.S. PATENT DOCUMENTS

| | | | | |
|---|---|---|---|---|
| 4,452,090 | A * | 6/1984 | Kou | G01F 1/668 |
| | | | | 73/861.28 |
| 5,275,060 | A * | 1/1994 | Lynnworth | G01F 1/662 |
| | | | | 73/861.18 |
| 5,437,194 | A * | 8/1995 | Lynnworth | G01F 1/662 |
| | | | | 73/861.27 |
| 5,515,733 | A * | 5/1996 | Lynnworth | G01F 1/662 |
| | | | | 73/644 |
| 5,905,693 | A * | 5/1999 | Dubois | H04R 1/00 |
| | | | | 367/173 |
| 6,032,538 | A * | 3/2000 | Rickman | G01L 19/0636 |
| | | | | 73/756 |
| 6,047,602 | A * | 4/2000 | Lynnworth | G01F 1/662 |
| | | | | 73/632 |
| 7,513,158 | B2 * | 4/2009 | Watanabe | G01H 11/06 |
| | | | | 73/584 |
| 7,726,192 | B2 * | 6/2010 | Okuda | B60Q 1/0023 |
| | | | | 73/587 |
| 7,775,110 | B2 * | 8/2010 | Okuda | G01H 11/08 |
| | | | | 73/587 |
| 10,269,336 | B2 * | 4/2019 | Lin | G10K 11/002 |
| 2003/0164661 | A1 | 9/2003 | Pfeifer | |
| 2006/0224298 | A1 * | 10/2006 | Lang | G01F 1/72 |
| | | | | 701/114 |
| 2009/0289528 | A1 * | 11/2009 | Voss | B06B 3/00 |
| | | | | 310/351 |
| 2010/0011866 | A1 * | 1/2010 | Van Klooster | G10K 9/22 |
| | | | | 73/644 |
| 2011/0061452 | A1 * | 3/2011 | King | G01Q 60/32 |
| | | | | 73/105 |
| 2011/0080803 | A1 * | 4/2011 | Vu | G01V 1/46 |
| | | | | 367/32 |
| 2012/0272923 | A1 * | 11/2012 | Stephens | A01K 15/021 |
| | | | | 119/719 |
| 2014/0165740 | A1 * | 6/2014 | Speidel | B06B 1/0685 |
| | | | | 73/861.28 |
| 2018/0061390 | A1 * | 3/2018 | Lin | G10K 11/002 |

FOREIGN PATENT DOCUMENTS

| | | |
|---|---|---|
| DE | 10 2009 046 144 A1 | 5/2011 |
| DE | 10 2009 046 145 A1 | 5/2011 |
| DE | 10 2010 064 117 A1 | 6/2012 |
| DE | 20 2013 101 798 U1 | 9/2014 |
| DE | 10 2015 106 352 A1 | 10/2016 |
| EP | 1 046 886 A1 | 10/2000 |
| EP | 1 096 237 A2 | 5/2001 |
| EP | 1 340 964 A1 | 9/2003 |
| EP | 2 148 322 A2 | 1/2010 |
| WO | 2016/169729 A1 | 10/2016 |

OTHER PUBLICATIONS

International Search Report, EPO, The Netherlands, dated Jul. 14, 2016.

Office Action dated Mar. 1, 2019, issued in corresponding Chinese application No. 201680021452.5.

* cited by examiner

ARRANGEMENT AND ULTRASONIC, FLOW MEASURING DEVICE

TECHNICAL FIELD

The present invention relates to an arrangement for transferring signals into a gaseous or liquid medium, and to an ultrasonic, flow measuring device

BACKGROUND DISCUSSION

An arrangement of an ultrasonic transducer with a filter element is known from European patent, EP 1 340 964 B1. This arrangement has, however, a signal radiating bending plate, whose edges feed body sound into the filter element. In this way, the ultrasonic signal is, indeed, centered in the middle, but the radiating area is very small. Additionally, a radial support of the filter element and an arrangement in a housing are not shown.

SUMMARY OF THE INVENTION

It is, consequently, an object of the present invention is to arrange the filter element in a housing, e.g. a measuring tube nozzle, with a subsegment, which is sealed to medium and in which body sound is not transferred at sealing locations.

The present invention achieves this object by an arrangement which includes a housing wall, an ultrasonic transducer and a damping element with a longitudinal axis, which damping element connects the ultrasonic transducer with the housing wall, wherein the ultrasonic transducer has a medium-contacting surface, from which ultrasonic signals are transferred into a gaseous or liquid medium, and wherein the damping element is provided between the ultrasonic transducer and the housing wall for body sound damping, and wherein the damping element has at least one, especially a number of, oscillatory nodes.

According to the invention, there is arranged between the damping element and the housing wall at least a first sealing ring, which is positioned at a height of an oscillatory node.

The terminology, ultrasonic transducer, refers preferably not exclusively to an ultrasound producing element. Thus, the terminology, ultrasonic transducer, is not limited exclusively to piezoelements or other ultrasound producing elements, but, instead, can also comprise the region of the arrangement, through which the ultrasonic signal must traverse before entry into the medium. The terminology, ultrasonic transducer, thus includes a surface, where an ultrasonic signal on a predetermined signal path is given off to the measured medium. All layers and components located between the ultrasound producing element and this surface are part of the ultrasonic transducer. The terminology, ultrasonic transducer, includes, thus, elements, involved in bringing an ultrasonic signal to the measured medium. These can comprise e.g. one or more coupling layers or matching layers. Especially preferably, e.g., a part of the ultrasonic transducer can be a metal end piece, from which an ultrasonic signal is transferred into a gaseous or liquid medium. Especially preferably, this metal end piece is joined with the damping element.

Ultrasonic signals are transferred from the surface into a gaseous or liquid medium. In the case of a flow measuring device, the medium can be a measured medium, or, in the case of fill level measurement, e.g. air.

The housing wall can be e.g. a nozzle on a measuring tube of an ultrasonic, flow measuring device. The nozzle forms, in such case, the housing for the ultrasonic transducer. The housing can, however, also belong to a fill-level measuring device fixedly or releasably connected with a tank.

The damping element can also be referred to as a bandpass filter. It serves for body sound damping, respectively body sound decoupling from the housing wall. The damping element is preferably embodied hollow cylindrically and includes an end face adjoined to the ultrasonic transducer by means of an interface.

Oscillation nodes of a standing wave are known per se. It is, consequently, understandable for those skilled in the art that corresponding oscillatory nodes form in the case of action of body sound, thus during operation of the ultrasonic transducer. As regards height, that means that the sealing ring is arranged at the same axial position along the longitudinal axis of the damping element as the oscillatory node and is spaced radially from the longitudinal axis.

It has been found that a positioning of a sealing ring not, for instance, at the position with the greatest oscillation amplitude but, instead, at the position of an oscillatory node enables a reduced lateral transfer of body sound to the housing wall. At the same time, a mechanical support of the damping element in the region of the lateral surface of the damping element is assured.

The damping element has advantageously a hollow-cylindrical and rotationally symmetric, basic form, so that a uniform standing wave forms upon axial introduction of body sound.

In order to achieve further advantageous canceling of body sound, the damping element sits advantageously terminally on a torus or on a spherically shaped body.

For better lateral support of the damping element, the arrangement advantageously additionally has between the damping element and the housing wall a sealing element, especially a rotationally symmetric sealing element, which extends over a region of at least 20% of the length of the damping element between the damping element and the housing wall, wherein the first sealing ring is arranged between the sealing element and the damping element.

In order to achieve prevention of lateral sound transfer at two locations, the arrangement advantageously has a second sealing ring, which is arranged between the sealing element and the housing wall at a height of an oscillatory node of the damping element.

A toroidal shape is especially favorable for canceling sound, since the sound waves are scattered uniformly in all directions. Therefore, the sealing ring has, advantageously, the profile of a round cord.

An especially effective canceling of body sound on a sound path extending longitudinally through the damping element is then achieved, when the damping element has at least one, preferably at least two, annular grooves. Above and below the annular groove, especially, however, between the annular grooves, an annular mass segment can be provided.

The arrangement includes in a terminal region of the damping element a closed hollow space, wherein the first sealing ring is provided, in order to prevent entry of measured medium into the hollow space. Arranged in this hollow space can be e.g. the connection lines for the sound producing element of the ultrasonic transducer. The connection lines are, thus, correspondingly protected from the measured medium.

The hardness of the first and/or of the second sealing ring amounts, according to DIN EN ISO 868 and/or DIN ISO 7619-1, to 60-80 ShA, preferably 65-75 ShA. The usual Shore-A test method for soft elastomers is generally known and is applied for measuring the aforementioned Shore hardnesses.

The material of the sealing ring is preferably a silicon-based elastomeric synthetic material, especially silicone.

The arrangement of the invention can be provided in a field device of process measurements technology, especially in an ultrasonic, flow measuring device for measuring gaseous media. The ultrasonic, flow measuring device includes a measuring tube, on which an arrangement as claimed in claim 1 is mounted.

The flow measurement can occur by means of the Doppler principle using only one arrangement or by means of the travel-time difference principle using two arrangements.

Alternatively, the arrangement can also be applied in a fill-level measuring device, wherein the measuring tube is, in such case, most often replaced by a container—e.g. a tank or a silo.

Also other field devices from the field of process measurements technology can use the arrangement.

BRIEF DESCRIPTION OF THE DRAWINGS

The present invention will now be explained in greater detail based on the appended drawing, the figures of which show as follows.

DETAILED DISCUSSION IN CONJUNCTION WITH THE DRAWINGS

The present arrangement can be applied both in the case of fill level measuring devices as well as also in the case of flow measuring devices. In the following, however, the construction, operation and advantages resulting therefrom will be described primarily for an ultrasonic, flow measuring device. The arguments can, however, predominantly also be applied to ultrasonic, fill level measurement.

Ultrasonic, flow measuring devices are widely applied in process and automation technology. They permit simple determination of volume flow and/or mass flow of a measured medium in a pipeline. Known ultrasonic, flow measuring devices work frequently according to the travel-time difference principle. In the case of the travel-time difference principle, the different travel times of ultrasonic waves, especially ultrasonic pulses, so-called bursts, are evaluated as a function of the flow direction of the liquid. For this, ultrasonic pulses are sent at a certain angle to the tube axis both with as well as also counter to the flow. From the travel-time difference, the flow velocity, and therewith, in the case of known diameter of the pipeline section, the volume flow, can be determined.

The ultrasonic waves are produced and received with the assistance of so-called ultrasonic transducers. For this, ultrasonic transducers are connected solidly with the tube wall of the relevant pipeline section. This device type is known to those skilled in the art also as an inline ultrasonic flow measurement device. Also clamp-on ultrasonic, flow measuring systems exist, which are placed, e.g. secured, externally on the measuring tube. Clamp-on ultrasonic, flow measuring devices are, however, not subject matter of the present invention Ultrasonic transducers have, normally, an electromechanical transducer element, e.g. one or more piezoelectric elements.

Both in the case of clamp-on systems, as well as also in the case of inline systems, the ultrasonic transducers are arranged on the measuring tube in a shared plane, either on oppositely lying sides of the measuring tube, in which case the acoustic signal then travels, projected on a tube cross section, once along a secant through the measuring tube, or on the same side of the measuring tube, in which case the acoustic signal is then reflected on the oppositely lying side of the measuring tube, whereby the acoustic signal traverses the measuring tube two times along the secant projected on the cross section through the measuring tube.

Figure 1:
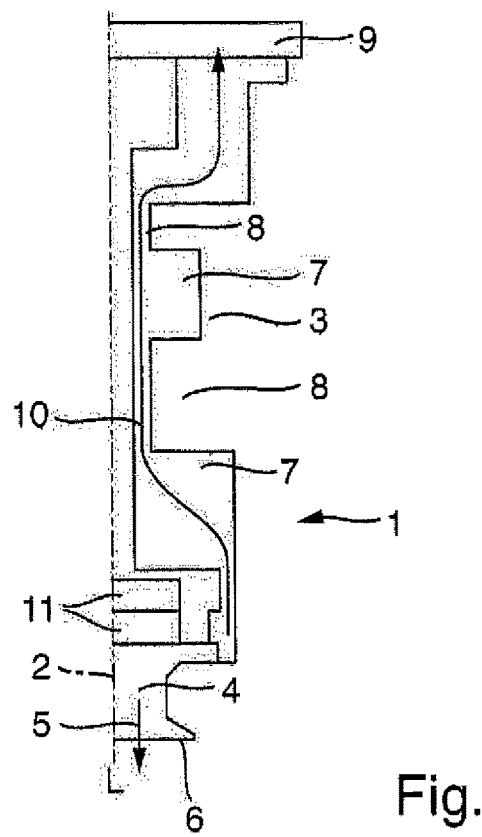
FIG. 1 is an arrangement not of the invention comprising an ultrasonic transducer and a damping element.

In the concrete example of an embodiment of FIG. 1, an arrangement 1 is embodied with a corresponding ultrasonic transducer 2 having two electromechanical transducer elements 11, especially two piezo elements, arranged on top of one another. It is, however, also possible to provide only one transducer element at the same location. Ultrasonic transducer 2 includes additionally an end piece 4 having a medium-contacting surface 6. At this surface 6, the ultrasonic waves produced by the one or more electromechanical transducer elements 11 are given off to a measured medium.

End piece 4 shown in FIG. 1 includes a pedestal, which is in contact, especially in Shape-interlocking contact, with the electromechanical transducer elements 11. Furthermore, the end piece 4 includes a bending plate 5 having the medium-contacting surface 6.

The pedestal of the end piece 4 includes an interface to a damping element 3. This damping element 3 is embodied as a cylindrical body with at least two annular grooves 8 extending parallel to one another. The interface between the ultrasonic transducer 2 and the damping element 3 can be embodied e.g. as a welded connection.

Arranged between the interface and a first of the two annular grooves 8 is a first annular mass segment 7, which has a greater wall thickness, especially a wall thickness at least twice as thick as that of the first of the two annular grooves 8.

Arranged between the two annular grooves 8 is, additionally, a second annular segment 7, which has a greater wall thickness, especially a wall thickness at least twice as thick as that of the annular grooves 8.

The damping element 3 has another interface, where the damping element 3 is affixed to the wall 9 of a housing or tube. FIG. 1 shows schematically additionally the path of the body sound, which travels through the damping element and which is significantly lessened by the illustrated damping element 3. So long as the arrangement shown in FIG. 1 is only terminally affixed, the arrangement provides a satisfactory decoupling of the connection location, thus of the tube or of the housing from the ultrasonic transducer. In the flow field of application or also in other fields of application, it can, however, be the case that the arrangement is arranged set back in a housing or a pipeline. This is e.g. the case for flow measurement, where the arrangement 1, i.e. the sensor element, can be arranged set back in a terminally closed nozzle or similar apparatus, in order that the flow is not to strongly disturbed.

In the case of such arrangements, in the case of a purely terminal arrangement, contaminants can collect in the region between the housing wall and the damping element. Therefore, it is prudent to provide in these regions sealing elements, thus sealing rings and/or other space filling sealing elements, in order to seal off the intermediate region between the housing wall and the damping element. The problems resulting therefrom and their solutions will now be discussed in greater detail based on FIGS. 2-6.

Figure 2:
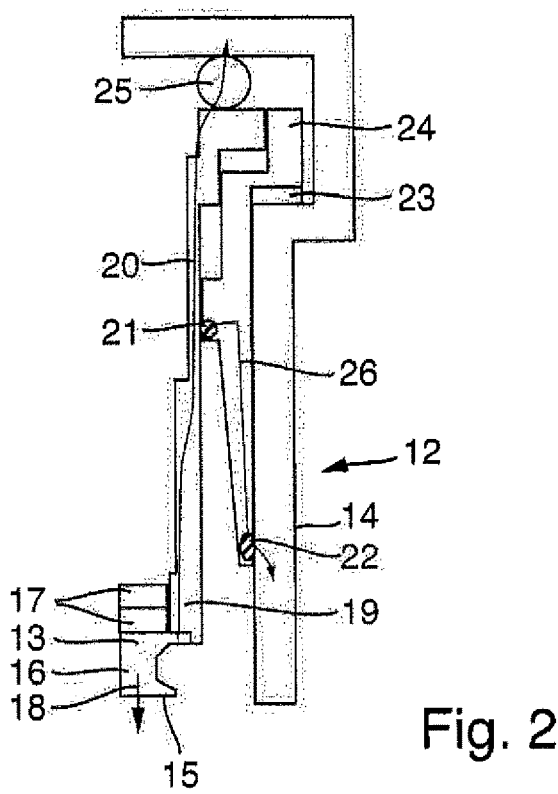
FIG. 2 is a first arrangement of the invention comprising an ultrasonic transducer and a damping element.

FIG. 2 shows an example of an embodiment of an arrangement 12 of the invention for producing and/or receiving an ultrasonic signal. The arrangement includes an ultrasonic transducer 13, a damping element 19, a sealing element 24 and a housing wall 14.

Ultrasonic transducer 13 is embodied analogously to that in FIG. 1. It includes two electromechanical transducer elements 17, especially two piezoelements, arranged on top of one another. Ultrasonic transducer 13 includes additionally an end piece 16 with a pedestal and a bending plate 18. Bending plate 18 has a medium-contacting surface 15, from which the ultrasonic signal is radiated into the measured medium.

Following the ultrasonic transducer 13 is a damping element 19, which is connected with the ultrasonic transducer 13 via an interface. The damping element is cylindrically constructed and has in contrast with the example of an embodiment of FIG. 1 no annular grooves and ring segments. The wall thickness of the damping element 19 varies, indeed, in some sections, however, without that annular grooves result therefrom.

The damping element rests terminally on a spherically shaped body 25 or on a torus, which is arranged between the mentioned damping element and the housing wall 14. The terminology, spherical, in the sense of the present invention, includes also deviations from the ideal circular shape and means, in general, bodies with concave, especially strongly concave, shape. Also, a partial flattening of a section of the body can be present.

Arranged laterally, thus between the cylindrical surface of the damping element 19 and the housing wall 14, is a sealing element 24. This sealing element 24 is shape-interlocked with the housing wall 14 in certain regions and includes likewise a shape interlocking connection with the damping element 19 in certain regions. Also a material bonded, e.g. welded, connection can be present at these shape-interlocking connections.

Additionally a sound path 20 is shown, which extends along and through the damping element.

Arranged between the sealing element 24 and the housing wall 14 in the region of a sharp bend is a further body-sound damping element 23. Arranged between the sealing element 24 and the damping element 19 as well as also between the sealing element 24 and the housing wall 14 are seals 21, 22, especially sealing rings. The positioning of these sealing rings 21 and 22 is decisive for the course of the body sound within the arrangement.

Two sound paths 20 and 26 are present in FIG. 2. Sound path 20 is the ideal sound path for body sound removal, so that it does not reach the housing wall 14. In order, however, to avoid a penetration of measured medium into the intermediate space between damping element 19 and housing wall 14 and for additional improvement of the mechanical stability of the damping element 19, a sealing element 24 is provided, which fills out the gap between the damping element 19 and the housing wall 14. Via this sealing element 24, however, body sound can also be transferred to the housing wall 14 via a sound path 26.

By an optimal placing of sealing bodies, thus of the sealing element 24 and the sealing rings 21, 22, however, transfer of body sound via the sound path 26 can be prevented.

The optimal placing of one or more sealing elements will now be explained in greater detail based on FIGS. 3-6.

Figure 3:
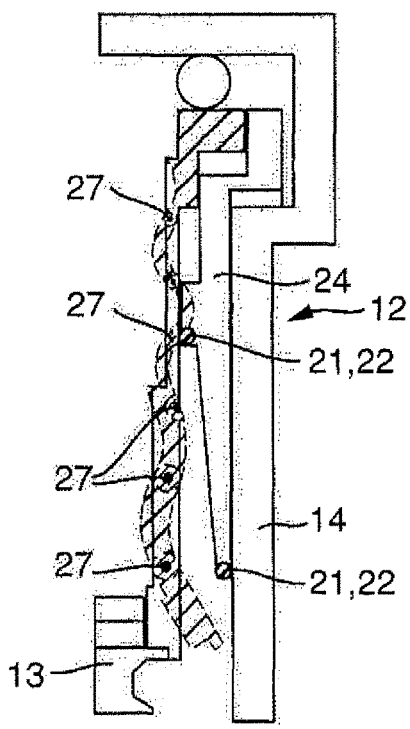
FIG. 3 is a schematic representation of the body sound oscillations of the damping element of FIG. 2.
Figure 4:
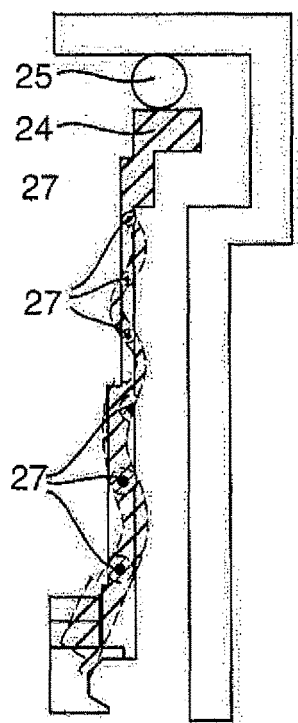
FIG. 4 is another schematic representation of the body sound oscillations of the damping element of FIG. 2.

FIG. 3 shows oscillatory behavior of the damping element 19 in the case of transporting a body sound signal. Shown is that the wall of the damping element assumes in the axial direction the form of a standing wave and that individual regions have a strong oscillation amplitude, while other regions are located in the resting position and execute virtually no or only small movements in the direction perpendicular to the longitudinal axis. These others regions are called oscillation nodes 27.

For a minimized sound transfer, it has proved to be favorable that one one or more sealing rings be emplaced at such an oscillation node 27.

FIG. 3 shows a sealing ring 21 arranged between the sealing element 24 and the damping element 19 at a height of a node 27, thus at the axial position of a node 27. It has been found that the placing of a sealing ring 21 at a node 27 enables an essentially smaller sound transfer via the above-described, undesired sound path 26.

Furthermore, also a sealing ring 22 is arranged between the sealing element 24 and the housing wall 14, also at a height of an additional node, thus at the axial position of the additional node 27. The specifications refer, of course, to the position of the node of the damping element 19 in the resting position.

FIG. 4 shows again the damping element 19 without any sealing element 24. The torus or the spherically shaped element 25, on which the damping element sits, serves, in such case, preferably as a low-pass filter, especially for axial modes.

Figure 5:
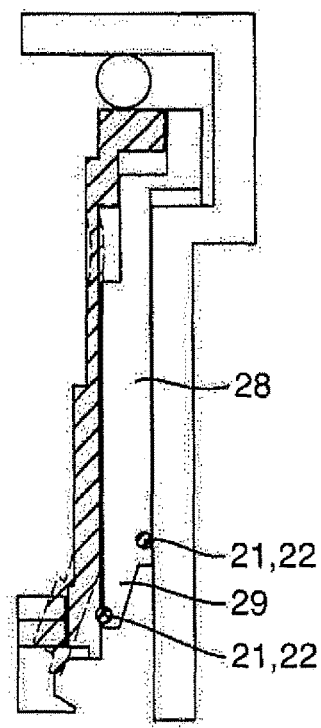
FIG. 5 is a schematic representation of the body sound oscillations of an additional embodiment of a damping element not of the invention.

FIG. 5 shows an example of an embodiment not of the invention, in which the sealing rings 21 and 22 are not positioned at heights of nodes. In the case of this example of an embodiment, compared with the example of an embodiment of FIG. 3, significant body sound is transferred to the housing wall.

Figure 6:
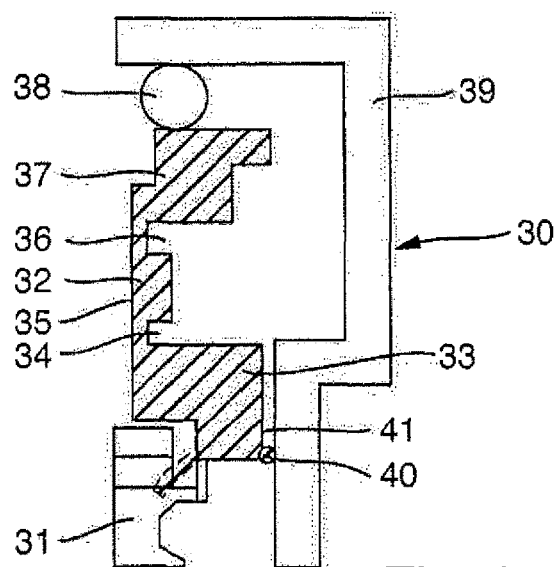
FIG. 6 is a schematic representation of the body sound oscillations of a second embodiment of a damping element of the invention.

Of course, the invention can also be presented in other examples of embodiments. Thus, FIG. 6 shows a further example of an embodiment of an arrangement 30 of the invention with an ultrasonic transducer 31, a damping element 32 and a housing wall 39 as well as an intermediately lying sealing ring 40 arranged at a height of a node.

Furthermore, the damping element includes, analogously to the damping element of FIG. 1, two annular grooves 34 and 36 as well as a number of mass segments 33, 35, 37. These have a greater volume with reference to the total volume of the damping element than the annular mass segments of the damping element of FIG. 1. Analogously to the examples of embodiments of FIGS. 2-5, additionally a torus or a spherically shaped body 38 is arranged terminally on the damping element 32.

Of course, many other examples of embodiments are implementable in the context of present invention. Therefore, the subject matter of the present invention is not limited to the above-described examples of embodiments.

In general, the arrangement of the invention can be constructed as one piece or multipiece. The damping element and the ultrasonic transducer are rotationally symmetric and are of metal. In such case, the end piece can preferably be of stainless steel or titanium. The damping element is composed preferably of stainless steel.

The invention claimed is:

1. An arrangement, comprising:
   a housing wall;
   an ultrasonic transducer; and
   a damping element with a longitudinal axis, which damping element connects said ultrasonic transducer with said housing wall, wherein:
   said ultrasonic transducer has a medium-contacting surface, from which ultrasonic signals are transferred into a gaseous or liquid medium;
   said damping element is provided between said ultrasonic transducer and said housing wall for body sound damping; and said damping element has at least one, especially a number of, oscillatory nodes characterized in that there is arranged between said damping element and said housing wall at least a first sealing ring, which is positioned at a height of an oscillatory node.

2. The arrangement as claimed in claim 1, wherein:
   said damping element has a hollow-cylindrical and rotationally symmetric, basic form.

3. The arrangement as claimed in claim 1, wherein:
   said damping element sits terminally on a torus or on a spherically shaped body.

4. The arrangement as claimed in claim 1, further comprising:
   between said damping element and said housing wall a sealing element, especially a rotationally symmetric sealing element, which extends over a region of at least 20% of the length of said damping element between said damping element and said housing wall, wherein: said first sealing ring is arranged between said sealing element and said damping element.

5. The arrangement as claimed in claim 4, further comprising:
   a second sealing ring, which is arranged between said sealing element and saud housing wall at a height of an oscillatory node of said damping element.

6. The arrangement as claimed in claim 1, wherein:
   said first and/or said second sealing ring has a round cord profile.

7. The arrangement as claimed in claim 1, wherein:
   said damping element has at least one, preferably at least two, annular grooves.

8. The arrangement as claimed in claim 1, further comprising:
   in a terminal region of said damping element a closed hollow space, wherein:
   said first sealing ring is provided, in order to prevent entry of medium into the hollow space.

9. The arrangement as claimed in claim 1, wherein:
   the hardness of said first and/or of said second sealing ring amounts, according to DIN EN ISO 868 and/or DIN ISO 7619-1, to 60-80 ShA, preferably 65-75 ShA.

10. The arrangement as claimed in claim 1, wherein:
    the material of said sealing ring is preferably a silicon-based elastomeric synthetic material, especially silicone.

11. An ultrasonic, flow measuring device comprising at least one, especially two, arrangements, as claimed in claim 1.

* * * * *